United States Patent [19]

Gazda

[11] 4,007,007
[45] Feb. 8, 1977

[54] APPARATUS FOR DECONTAMINATING LIQUIDS OF BACTERIA

[76] Inventor: Hans Otto Ernst Gazda, Anton Kriegerg. 155, A-1238 Vienna, Austria

[22] Filed: Feb. 22, 1974

[21] Appl. No.: 444,803

[52] U.S. Cl. .............................. 21/102 R; 99/451; 426/237
[51] Int. Cl.² .......................................... A61L 3/00
[58] Field of Search ............... 233/1 R, 15, 16, 17, 233/21, 26, 27, 28, 29; 426/237, 665, 238; 21/91, 102 R; 99/460, 451

[56] References Cited

UNITED STATES PATENTS

| 2,339,735 | 1/1944 | Smith | 21/91 |
|---|---|---|---|
| 3,269,546 | 8/1966 | Kainz | 233/28 X |
| 3,547,547 | 12/1970 | Anderson | 233/26 X |
| 3,594,115 | 7/1971 | Wesley et al. | 21/102 R |
| 3,759,666 | 9/1973 | Hill | 233/26 X |
| 3,810,576 | 5/1974 | Polson | 233/37 |
| 3,876,373 | 4/1975 | Glyptis | 21/102 R |

Primary Examiner—George H. Krizmanich
Attorney, Agent, or Firm—Karl F. Ross; Herbert Dubno

[57] ABSTRACT

An apparatus for the decontamination of a bacteria-containing liquid comprises a pair of vertically spaced juxtaposed horizontal disks whose confronting faces are formed with mutually registering alternating annular grooves and lands of trapezoidal profile to define a succession of horizontally spaced compartments communicating through passages between them. When the disk is rotated with a peripheral speed of between 200 and 800 m/sec., bacteria contained in the liquid is destroyed.

1 Claim, 3 Drawing Figures

VOLTAGE SOURCE

APPARATUS FOR DECONTAMINATING LIQUIDS OF BACTERIA

At present, primarily liquids such as milk, fruit juices or the like, are decontaminated from bacteria by pasteurization and sterilization. However, even in cold storage, pasteurised milk will only keep for a few days since imperfections in the taste are still caused very quickly by psychrophylic bacteria. Moreover pasteurization gives a reduction in bacteria of only 99.8% at best.

Sterilized milk which will keep for a longer period of time and may be transported under normal conditions, but its nutritive value is reduced and the natural character of the milk is changed by destroying flavor and aroma. Depending on the method used, to a greater or lesser extent sterilization brings about a decrease in the biological value, considerable destruction of vitamins and an intensive cooking or caramel taste.

At present a method is also used which has become known as bacteria centrifugation, in which the milk is centrifuged at 10,000g and above, thereby throwing the bacteria, in particular the bacillus spores, out of solution (U.S. Pat. No. 3,217,982).

However, such centrifugation causes economically unacceptable losses of protein and fat which are deposited with the centrifugation sediment. Furthermore, bacteria-centrifuged milk still requires pasteurization since it can contain residual pathogenic bacteria.

It is an object of the invention to provide an apparatus and method whereby bacteria may be removed from liquids such as milk, fruit juices, medicinal solutions or the like by a mechanical process without requiring the application of heat and without substantial destruction of vitamins, flavoring agents, perfumes and other essential substances.

According to one aspect of the invention there is provided an apparatus for decontaminating liquids of bacteria, comprising a centrifuge have a rotary disc with an internal passage of varying cross sectional area extending radially outwardly from a liquid inlet to a liquid outlet whereby the liquid travels through said passage at a high velocity and with repeated substantial changes in acceleration so as to destroy bacteria present in the liquid.

According to a second aspect of the invention there is provided a method of decontaminating liquids of bacteria comprising subjecting the liquid to high velocity travel with abrupt changes in acceleration thereby to destroy bacteria present in the liquid.

The mechanical deactivation of bacteria is primarily achieved in the invention by the interaction of accelerative force, cavitation and stress in the structure of the cell membrane. The liquid from which bacteria are to be removed is exposed to enormous accelerations and decelerations and thus to alternating mechanical stresses.

The liquid pressure and speed reduces as it enters a region of expanded cross section. At high speed, the pressure is lower than at slow speeds. The resulting difference in the pressure which is related to speed by Bernouilli's equation, is the cause of structural changes in the protein molecules of the cells. When the pressure is increased, as a result of deceleration, the bubbles of milk condense and the liquid cavities collapse suddenly with nonelastic impact. Forces are thus released in the order of magnitude of $10^4$–$10^6$ atmospheres. For a water vapor bubble which collapses to 1/20th of its diameter during the condensation process, Lord Rayleigh discovered a pressure surge of 10,300 atmospheres.

Figure 2:
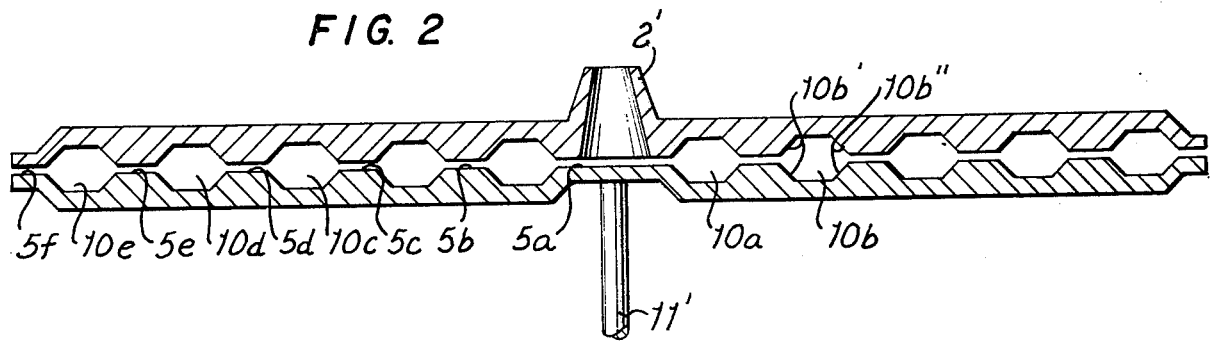
FIG. 2 is an axial section through an embodiment of the invention provided with five recesses in succession.
Figure 1:
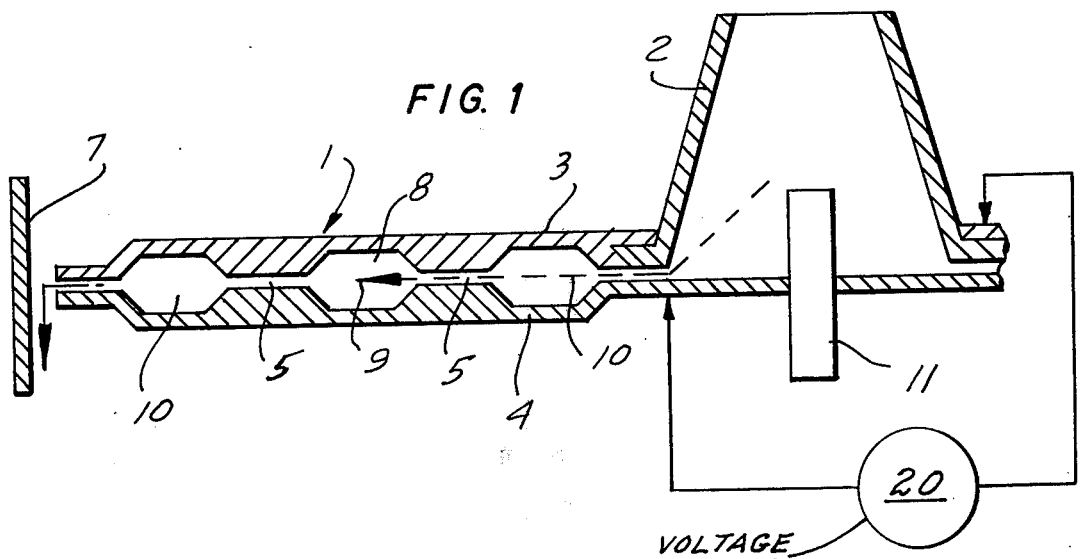
FIG. 1 is a diagrammatical sectional view of an apparatus according to the invention, not drawn to scale.
Figure 3:
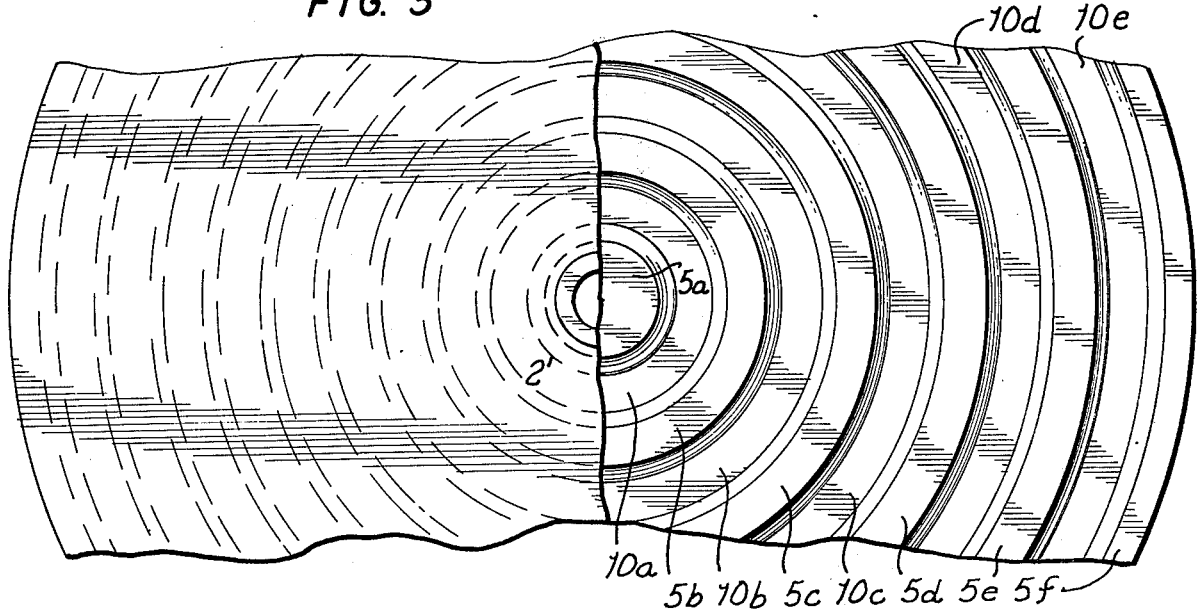
FIG. 3 is a plan view of the apparatus of FIG. 2 with the upper disk cut away at the right-hand side of this figure.

Th multiform oscillations inside the cells and the surrounding liquid are no longer in phase after a short distance has been traversed. Corresponding stress in the molecular system of the cell components occurs, which tears it at the weak points. The molecules lose their specific structures together with these bonds. The normal metabolic activity, growth and ability to replicate are suppressed.

Proteins form the main component of macromolecules. In the centrifuge for removing bacteria according to the invention, the latter are subjected to enormous strain due to their different molecular weights. In the centrifuge for removing bacteria, a high electrostatic charge develops, as the liquid from which bacteria is to be removed passes therethrough owing to friction on the edges of the passage. This charge, assisted by the high accelerative forces of the centrifuge causes a separation of the cations and anions. As a result, further stress on the structure occurs within the cells. This process may be further increased by applying a voltage, of approximately 70 volts.

Bacteria may be removed from the milk and it may also be homogenized in a single operation by the apparatus of the invention.

When milk is treated using the method and apparatus according to the invention it remains fresh both biologically and as regards taste and can be stored and transported to at least the same extent as sterilized milk.

One embodiment of the invention will now be described with reference to the drawing, the sole Figure of which is a diagrammatic sectional view of apparatus according to the invention (not to scale).

The apparatus shown in the drawing comprises a centrifuge consisting of two plates 3 and 4, located one above the other and forming a disc 1. The disc is located inside a collecting vessel indicated by the reference numeral 7. The plates 3 and 4 are separated by a distance forming a nozzle gap 5. Provided in each plate 3 and 4, on opposing sides, are several radially spaced grooves 8 or 9 which represent chamber-like extensions 10 of the nozzle gap 5. The extensions 10 are joined to the nozzle gap 5 by tapering surfaces. Connected to the upper plate 3 of the disc 1 is a filling pipe 2 through which the milk is supplied to the centrifuge. The disc 1 is rotated by a shaft 11. A voltage source 20 applies a voltage of about 70 volts across the plates.

In a practical embodiment of a centrifuge according to the drawing, the diameter of the disc is 600 mm and the speed of rotation is up to 20,000 r.p.m. The disc has a peripheral speed of up to 628 m/sec and the milk is accelerated up to 132, 600g. In this embodiment, the nozzle orifice has a width of 0.5 mm and the height of the chamber-like extension, twenty of which are located radially in line is 12 mm. At 10,000 r.p.m., the output is 30,000 liters per hour.

The appropriate speed, nozzle width and height, length and number of chamber-like extensions must be determined for each embodiment and according to the liquid from which bacteria is to be removed by empirical series tests. Preferably, the nozzle width should be between 0.1 and 1 mm and the chamber-like extensions, at least five of which should preferably be provided, normally have a height of between 5 and 20 mm. The peripheral speed of the centrifuge disc is preferably between 200 and 800 m/sec. FIG. 2 shows an embodiment of the invention in which the downwardly deriving inlet 2' distributes the liquid containing the micro-organisms to be destroyed to a first annular narrow radially outwardly extending gap 5a. The high velocity of the device forces the liquid through this gap which is constricted relative to the flow cross-section of the liquid distributing inlet 2' so that the liquid flow is sharply accelerated. As the liquid passes through this constriction it enters into an annular chamber 10a formed by confronting annular trapezoidal section recesses in the two plates and, in accordance with the dynamics of fluid flow, has a sharply reduced velocity, i.e. is greatly decelerated.

From the chamber 10a the liquid is forced to flow, by the centrifugal action, through the narrow passage 5b and again is accelerated sharply to be of increased velocity and enter the next chamber 10b wherein, as described with chamber 10a the velocity of the liquid is sharply reduced and hence the liquid is decelerated. In the successive passages 5c, 5d, 5e and 5f, the liquid is always accelerated while in chambers 10c, 10d and 10e, the velocity is reduced and the liquid is decelerated.

As noted above, the alternating accelerations and decelerations result in a breakdown of the structure of the micro-organism and is a sterilization of the liquid. The application of a voltage across the plates draws charged particles of the mircro-organism to the walls of the passages and chambers and hence increases the frictional engagement of the micro-organisms with the walls to further promote breakdown of the micro-organism structure. Furthermore, the electric field tends to bring about a separation of charges within the micro-organism and also promotes stressing thereof to facilitate breakdown.

The walls 10b' and 10b'' of the chambers, e.g. 10b, diverge outwardly and converge outwardly alternately, the deceleration of the liquid and the acceleration liquid taking place predominantly along these walls at which the flow cross-section is alternately increased and decreased.

What I claim is:

1. An apparatus for decontaminating bacteria-containing liquid comprising:
    a rotary disk formed by a pair of vertically spaced horizontal plates having juxtaposed faces formed with registering radially spaced relatively wide recesses and defining relatively narrow passages between said recesses for communicating between them, said recesses and passages being radially aligned;
    an inlet opening into an inner one of said passages for delivering said liquid to the interior of said disk;
    an outlet along the periphery of said disk for said liquid;
    means for rotating said disk at a peripheral speed sufficient to centrifugally displace said liquid at high velocity between said plates, said passages being sufficiently narrow and said recesses being sufficiently wide that said high velocity causes substantial changes in acceleration of said liquid at junctions of said passages with said recesses to destroy bacteria present in the liquid; and
    means for applying a voltage of approximately 70 volts to said plates.

* * * * *